United States Patent [19]
Drent

[11] Patent Number: 4,945,179
[45] Date of Patent: Jul. 31, 1990

[54] PROCESS FOR THE PREPARATION OF ESTERS OF CARBOXYLIC ACIDS AND CATALYTIC SYSTEM FOR USE THEREIN

[75] Inventor: Eit Drent, Amsterdam, Netherlands

[73] Assignee: Shell Oil Company, Houston, Tex.

[21] Appl. No.: 232,059

[22] Filed: Aug. 15, 1988

[30] Foreign Application Priority Data

Sep. 28, 1987 [GB] United Kingdom ............... 8722743

[51] Int. Cl.$^5$ ............................................. C07C 67/38
[52] U.S. Cl. ..................................... 560/233; 558/441; 560/105; 560/114; 560/155; 560/175; 560/179; 560/187; 560/226; 260/410.9 R
[58] Field of Search ............... 560/233, 105, 114, 155, 560/175, 179, 187, 226; 558/441; 260/410.9

[56] References Cited

U.S. PATENT DOCUMENTS

| | | | |
|---|---|---|---|
| 3,040,090 | 6/1962 | Alderson | 560/233 |
| 3,168,553 | 2/1965 | Slaugh | 260/497 |
| 3,646,116 | 2/1972 | McClure | 560/233 |
| 3,944,604 | 3/1976 | Hershman | 560/233 |
| 4,238,357 | 12/1980 | Pesa | 560/233 |
| 4,431,593 | 2/1984 | Jenck | 560/233 |
| 4,451,407 | 5/1984 | Pesa | 560/233 |
| 4,451,679 | 5/1984 | Knifton | 568/909 |
| 4,681,707 | 7/1987 | Alper | 560/233 |

OTHER PUBLICATIONS

J. Molecular Catalysis, 40, (1987), pp. 243–254.

Primary Examiner—Michael L. Shippen

[57] ABSTRACT

Process for the preparation of esters of carboxylic acids by contacting an olefinically unsaturated compound with CO and an alcohol, in the presence of (a) a ruthenium compound and (b) an iodide salt, LiBr and/or an onium bromide, with a molar ratio of CO to olefinically unsaturated compound $\leq 2.0$ being applied when "b" is an iodide salt.

9 Claims, No Drawings

PROCESS FOR THE PREPARATION OF ESTERS OF CARBOXYLIC ACIDS AND CATALYTIC SYSTEM FOR USE THEREIN

FIELD OF THE INVENTION

The invention relates to a process for the preparation of esters of carboxylic acids. The invention also relates to a catalytic system which may be used in this process.

BACKGROUND OF THE INVENTION

U.S Pat. No. 3,168,553 discloses a process in which olefins are carboxylated in the presence of a complex comprising a trialkylphosphine together with cobalt, ruthenium, rhodium or iridium. However, this process requires the use of high pressures, and its selectivity towards the desired product is often unsatisfactory. For instance, the carbonylation of ethylene in the presence of ethanol and $CO_2(CO)_8$ as the catalyst leads to the formation not only of ethyl propionate, but also of large quantities of by-products, such as diethyl ketone and acetaldehyde.

J. Molecular Catalysis 40 (1987) 243–254 concerns the synthesis of ketones and esters from olefins, carbon monoxide and alcohols by using ruthenium-iodide catalysts. In the carbonylation of ethylene with methanol, use of ionic iodides such as sodium iodide gives methyl propionate selectivity, using pressures of carbon monoxide and ethylene of 45 and 20 kg/cm$^2$, respectively.

It has now been found that by selecting a molar ratio of carbon monoxide to olefinically unsaturated compound below a certain value, the process results in a higher reaction rate and even in a higher selectivity to esters of carboxylic acids. Moreover, said known process can successfully be amended by using certain bromides.

SUMMARY OF THE INVENTION

The invention therefore provides a process for the preparation of esters of carboxylic acids which process comprises contacting an olefinically unsaturated compound with carbon monoxide and an alcohol in the presence of a catalytic system which may be prepared by combining the following components:
component (a)—a ruthenium compound, and
component (b)—an iodide salt, lithium bromide and/or an onion bromide, wherein a molar ratio of carbon monoxide to olefinically unsaturated compound of not higher than about 2.0 is applied when component (b) is an iodide salt.

DESCRIPTION OF THE PREFERRED EMBODIMENT

The selectivity to a certain compound, expressed in a percentage, is defined herein as $100 \times c:d$ in which "c" is the amount of starting olefinically unsaturated compound that has been converted into that certain compound and "d" is the total amount of starting olefinically unsaturated compound that has been converted.

The "certain bromides" mentioned hereinbefore are lithium bromide and onium bromides. In the presence of lithium bromide and onium bromides, a molar ratio of carbon monoxide to olefinically unsaturated compound of not higher than 2.0 is preferably applied. Such molar ratios also result in a higher reaction rate and a higher selectivity to esters of carboxylic acids.

Amending the process of the present invention by replacing component (b) with, for example, lithium chloride, sodium bromide, calcium bromide, cobalt(II) bromide, zinc bromide, tin(IV) bromide or an onium chloride results in decreased reaction rates and/or decreased selectivities to esters of carboxylic acids.

According to a preferred embodiment of the present invention, a molar ratio of carbon monoxide to olefinically unsaturated compound in the range of from about 0.2 to about 2.0 is used.

The onium compounds as meant herein are derived from the elements of Groups VA and VIA of the Periodic Table of the Elements, i.e. from nitrogen, phosphorus, arsenic, antimony, sulfur, selenium and tellurium, and preferably from nitrogen and phosphorus. Those derived from nitrogen, phosphorus, arsenic and antimony are salts containing quadricovalent atoms with such atoms being bound to four hydrocarbon groups and those derived from sulfur, selenium and tellurium are salts containing tricovalent atoms with such atoms being bound to three hydrocarbon groups.

The iodide salt of component (b) is preferably an onium iodide or an iodide of an alkali metal, i.e. of lithium, sodium, potassium, rubidium or cesium, with lithium being preferred since it usually allows the highest reaction rates and highest selectivities to esters of carboxylic acids. The catalytic system contains two different components, i.e. component (a) and component (b) are not both ruthenium triiodide.

Among the iodides and bromides, the bromides are preferred because they are generally less corrosive.

Very good results have been obtained with iodides and bromides derived from quaternary phosphonium hydroxides, particularly those derived from quaternary alkylphosphonium hydroxides having less than about 20 and, more particularly, less than about 10 carbon atoms per alkyl group.

If desired, the process according to the present invention may be carried out in the presence of a crown ether which solubilizes the cation of the iodide salt or the lithium ion. An example of a crown ether is 1,4,7,10,13,16-hexaoxacyclooctadecane, also known under the name "18-crown-6". This compound may be prepared as described in "Synthesis" 1976, pages 515 and 516.

Another feature of the present invention is that the catalytic system is very stable and, therefore, can be used for a long time. No plating out of metallic ruthenium has been observed. Replacement of component (a) with a palladium compound would result in plating out of metallic palladium.

Examples of suitable ruthenium compounds are ruthenium oxides and ruthenium salts. Very good results have been obtained with compounds of trivalent ruthenium, particularly ruthenium tri(acetylacetonate). Other examples of suitable ruthenium compounds are ruthenium tribromide, ruthenium trichloride and triruthenium dodecacarbonyl. Component (a) may be a mixture of ruthenium compounds. Amending the present process by using ruthenium tri(acetylacetonate) and deleting component (b) results in hardly any reaction. Amending the present process by using ruthenium trichloride and deleting component (b) results in the formation of diethyl ketone.

The quantity of component (a) used may vary within wide ranges and is generally in the range between about $10^{-6}$ and about $10^{-1}$ and preferably between about $10^{-5}$ and about $10^{-2}$ gram-atom ruthenium per mol starting olefinically unsaturated compound.

The quantity of component (b) may also vary within wide ranges. Component (b) is preferably present in a quantity in the range of from about 0.1 to about 100 and particularly from about 0.5 to about 20 equivalents per gram-atom of ruthenium.

The process according to the present invention may be carried out at a temperature and a pressure which are not critical and may vary within wide ranges. The process is preferably carried out at a temperature in the range of from about 100° C. to about 250° C., preferably from about 125° C. to about 225° C. and pressure in the range of from about 5 to about 200 bar, preferably from about 25 bar to about 100 bar, but temperatures above about 250° C. or below about 100° C. or pressures above about 200 bar or below about 5 bar may also be used, if desired.

The olefinically unsaturated compound may be an unsubstituted or a substituted alkene or cycloalkene preferably have 2 to about 30, and in particular 2 to about 20, carbon atoms and preferably 1 to about 3 double bonds per molecule. The alkene or cycloalkene may be substituted, for instance, with one or more halogen atoms or cyano, ester, alkoxy, hydroxy, carboxy or aryl groups. If the substitutents are not inert under the reaction conditions, the carboxylation reaction may be accompanied with other reactions. For instance, the carboxylation of allyl alcohol is accompanied with esterification of the hydroxy group. Examples of suitable olefinic compounds are ethene, propene, 1-butene, 2-butene, isobutene, the isomeric pentenes, hexenes, octenes and dodecenes, 1,5-cyclooctadiene, cyclododecene, 1,5,9-cyclododecatriene, allyl alcohol, methyl acrylate, ethyl acrylate, methyl methacrylate, acrylonitrile, acrylamide, N,N-dimethylacrylamide, vinyl chloride, allyl chloride, acrolein, oleic acid, methyl allyl ether and styrene. Preference is given to alkenes having 1 to about 5 carbon atoms per molecule, in particular to ethylene and propylene. The use of ethylene is most preferred, with propionates being obtained with a very high selectivity.

The alcohols used in the process according to the invention may be aliphatic, cycloaliphatic or aromatic and may be substituted with one or more substituents which do not interfere with the reaction, such as mentioned hereinbefore in connection with the olefinically unsaturated compounds to be used as starting material. The alcohol may therefore also be a phenol. The alcohols preferably contain not more than about 20 carbon atoms per molecule. Examples of suitable alcohols are methanol, ethanol, propanol, isobutanol, tert-butyl alcohol, stearyl alcohol, benzyl alcohol, cyclohexanol, allyl alcohol, chlorocapryl alcohol, ethylene glycol, 1,2-propanediol, 1,4-butanediol, glycerol, polyethylene glycol, 1,6-hexanediol, phenol and cresol.

Special preference is given to alkanols having in the range of from 1 to about 10 carbon atoms per molecule. If the alcohol has more than one hydroxy group, different products may be formed, depending on the molar ratios existing between the reagents. For instance, depending on the quantity of olefinically unsaturated company used, either a mono-ester or a di-ester may be produced from glycol. The process according to the present invention is particularly suitable for the preparation of methyl propionate, starting from ethylene, carbon monoxide and methanol, methyl propionate being an important solvent.

In the process according to the invention, the carbon monoxide may be used pure or diluted with an inert gas, such as nitrogen, noble gases or carbon dioxide. Generally, the presence of more than about 10% by volume of hydrogen is undesirable. Preference is usually given to the use of carbon monoxide or a carbon monoxide containing gas which contains less than about 5% by volume of hydrogen.

The molar ratio of the olefinically unsaturated compound to alcohol is not critical. The molar ratio between hydroxy groups and olefinic double bonds any lie for instance between about 0.1:1 and about 10:1. When using a mono-olefin and a monohydric alcohol, preference is usually given to the use of an excess of the hydroxy compound mentioned. However, when using a polyhydric alcohol to prepare a polyester, it will generally be necessary to use an excess of olefinically unsaturated company.

The process according to the invention may be carried out batchwise, continuously or semi-continuously. Generally, there is no need for the use of a solvent since usually there will be an excess of one of the reactants such as, for example, the alcohol, which may serve as a solvent as well. If required, however, a solvent may be used, for instance diisopropyl sulfone, tetrahydrothiophene 1,1-dioxide (also referred to as sulfolane), acetone, chloroform, methyl isobutyl ketone, diglyme (dimethyl ether of diethylene glycol) or diisopropyl ether. The primary reaction product of the carbonylation reaction may also be used as a solvent.

The reaction mixtures obtained may be subjected to suitable catalyst and product separating means comprising one or more such steps, for example, as stratification, solvent extraction, distillation, fractionation or adsorption. The catalytic system as well as unconverted starting compounds or solvent, if any, may be recycled, in part or entirely, to the reaction zone.

The invention, moreover, provides a catalytic system prepared by combining (a) a ruthenium compound and (b) lithium bromide and/or an onium bromide.

The following Examples which further describe the invention are illustrative and are not intended to be construed as limiting the invention. The experiments were carried out in a 300 ml magnetically stirred Hastelloy C autoclave ("Hastelloy" is a trade mark). The reaction mixtures obtained were analyzed by means of gas-liquid chromatography. The Examples are according to the present invention, the Comparative Experiments are not.

EXAMPLES 1–7 AND COMPARTIVE EXPERIMENTS A–I

The autoclave was charged with methanol (50 ml, 1.23 mol), ruthenium tri(acetylacetonate) (0.2 mmol) and compound (b), flushed with carbon monoxide, sealed, charged with carbon monoxide, charged with ethylene and heated to a temperature of 175° C. The Table hereinafter states which compound (b) was used, the amount in which this compound was used and the pressures of carbon monoxide and ethylene to which the autoclave was charged at ambient temperature. Sixteen experiments were carried out in this manner.

After a reaction time of 5 h, the autoclave was allowed to adopt ambient temperature and then opened for analysis of the reaction mixture. The Table hereinafter presents the reaction rates and the selectivity to methyl propionate.

A comparison between the Examples 1, 3 and 5, where a molar ratio carbon monoxide to ethylene of 1.0:1.0 was used with the Examples 2, 4 and 6, respectively, where this molar ratio was 2.0 shows that a lower molar ratio results in a higher reaction rate and a higher selectivity to methyl propionate.

Comparative Experiments A and B show that using lithium chloride and sodium bromide results in a low reaction rate.

Comparative Experiments C, D and E show that using calcium bromide, cobalt bromide and zinc bromide results in a selectivity to methyl propionate which is lower than 90%.

Comparative Experiments G, H and I show that lithium phosphate, sodium phosphate and nickel phosphate do not promote the carbonylation.

Example 7 shows that the presence of tetrabutylammonium iodide allows a high reaction rate and high selectivity to methyl propionate.

monoxide and ethylene were 25 bar each and the reaction mixture was kept for 5 h at a temperature of 175° C.

The reaction rate was 100 mol ethylene per gram-atom ruthenium per h, with selectivities to propionic aldehyde and diethyl ketone of 75% and 18%, respectively, with only traces of propionic acid.

EXAMPLE 9

An experiment was carried out as Example 1 using the following ingredients: methanol (50 ml), tetrabutylphosphonium bromide (2 mmol) ruthenium tri-(acetylacetonate) (0.2 mmol) propylene (30 ml).

The autoclave was flushed with carbon monoxide and charged with carbon monoxide until a pressure of 30 bar was obtained.

The reaction rate was 40 mol propylene per gram-

TABLE

| Example | Comparative Experiment | Compound (b) | amount mmol | Pressure, bar CO | Pressure, bar $C_2H_4$ | Reaction rate mol methyl propionate per gram-atom Ru per h | Selectivity, %, to methyl propionate |
|---|---|---|---|---|---|---|---|
| 1 | | LiBr | 2 | 20 | 20 | 175 | 97.4 |
| 2 | | LiBr | 2 | 30 | 15 | 130 | 94.3 |
| | A | LiCl | 2 | 20 | 20 | 10 | — |
| | B | NaBr | 2 | 20 | 20 | 40 | 92.7 |
| | C | $CaBr_2$ | 1 | 20 | 20 | 175 | 82.3 |
| | D | $CoBr_2$ | 1 | 20 | 20 | 145 | 82.8 |
| | E | $ZnBr_2$ | 1 | 20 | 20 | 120 | 89.4 |
| 3 | | $NaJ^{(1)}$ | 2 | 20 | 20 | 750 | 98 |
| 4 | | $NaJ^{(1)}$ | 2 | 30 | 15 | 370 | 97.4 |
| 5 | | tetrabutylophosphonium bromide | 2 | 20 | 20 | 175 | 97.8 |
| 6 | | tetrabutylophosphonium bromide | 2 | 30 | 15 | 60 | 96.6 |
| | F | methyltriphenylphosphonium chloride | 2 | 20 | 20 | 10 | — |
| | G | $Li_3PO_4$ | 2 | 20 | 20 | 0 | — |
| | H | $Na_3PO_4$ | 2 | 20 | 20 | 0 | — |
| | I | $Ni_3(PO_4)_2$ | 2 | 20 | 20 | 0 | — |
| 7 | | tetrabutylammonium iodide$^{(2)}$ | 2 | 20 | 20 | 740 | 98.4 |

$^{(1)}$reaction time 3 h
$^{(2)}$reaction time 1.5 h

EXAMPLE 8

An experiment was carried out as Example 1 with the difference that ruthenium tri(acetylacetonate) (0.2 mmol) was replaced with trirutheniumdodecacarbonyl (0.07 mmol).

The reaction rate was 180 mol methyl propionate per gram-atom ruthenium per h, with a selectivity to methyl propionate of 97.5%.

COMPARATIVE EXPERIMENT J

An experiment was carried out as Example 1 using the following ingredients: water (10 ml), ruthenium tri(acetylacetonate) (0.2 mmol), diglyme (40 ml), lithium bromide (2 mmol). The starting pressures of carbon monoxide and ethylene were 20 bar each and the reaction mixture was kept for 5 h at a temperature of 175° C.

The reaction rate was 100 mol ethylene per gram-atom ruthenium per h, with selectivities to propionic acid and diethyl ketone of 47% and 52%, respectively.

This experiment shows that propionic acid is not formed with a high selectivity.

COMPARATIVE EXPERIMENT K

An experiment was carried out as Example 1 using the following ingredients: water (10 ml), ruthenium tri(acetylacetonate) (0.2 mmol), diglyme (40 ml), sodium iodide (2 mmol). The starting pressures of carbon atom ruthenium per h, with selectivities to n-butyl butyrate and isobutyl butyrate of 45% and 55%, respectively.

I claim:

1. A process for the preparation of esters of carboxylic acids which process comprises contacting an olefinically unsaturated compound with carbon monoxide and an alcohol in the presence of a catalytic system is prepared by combining:
   component (a)—a ruthenium compound and
   component (b)—lithium bromide and/or an onium bromide, wherein a molar ratio of carbon monoxide to olefinically unsaturated compound of not higher than 2.0 is used.

2. The process of claim 1 wherein component (a) comprises ruthenium tri(acetylacetonate).

3. The process of claim 1 wherein component (b) is phosphonium bromide.

4. The process of claim 1 wherein said alcohol is an alkanol having not more than about five carbon atoms per molecule.

5. The process of claim 1 wherein a molar ratio of carbon monoxide to olefinically unsaturated compound in the range of from 0.2 to 2.0 is used.

6. The process of claim 1 wherein component (b) is present in a quantity in the range of from about 0.1 to about 100 equivalents per gram-atom of ruthenium.

7. The process of claim 1 wherein said process is carried out at a temperature in the range of from about 100° C. to about 250° C. and a pressure in the range of from about 5 bar to 200 bar.

8. The process of claim 1 wherein the olefinically unsaturated compound is an alkene having in the range of from 2 to about 30 carbon atoms per molecule.

9. The process of claim 8 wherein the alkene is ethylene.

* * * * *